(12) United States Patent
Russell et al.

(10) Patent No.: US 6,664,097 B2
(45) Date of Patent: Dec. 16, 2003

(54) **POLYNUCLEOTIDE ENCODING A *LACTOBACILLUS GASSERI* BETA-GLUCURONIDASE POLYPEPTIDE**

(75) Inventors: William Michael Russell, Madison, WI (US); Todd Robert Klaenhammer, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/862,660

(22) Filed: May 21, 2001

(65) Prior Publication Data

US 2003/0003562 A1 Jan. 2, 2003

Related U.S. Application Data

(60) Provisional application No. 60/206,372, filed on May 23, 2000.

(51) Int. Cl.$^7$ .............................. C12N 1/20; C12N 9/26; C12N 15/00; C07H 21/04
(52) U.S. Cl. .................. 435/252.3; 536/23.2; 536/23.7; 435/320.1; 435/201; 435/419; 435/325; 435/254.11; 435/252.9; 435/455; 435/468; 435/471
(58) Field of Search ................................ 536/23.2, 23.7; 435/471, 320.1, 201, 419, 325, 254.2, 252.3

(56) References Cited

PUBLICATIONS

Akao, Taiko, *Purification and Characterization of Glycyrrhetic Acid Mono–glucuronide α–D–Glucuronidase in Eubacterium sp. GLH*, Biol. Pharm. Bull., vol. 22, No. 1, pp. 80–82 (1999).

Akao, Taiko, *Competition in the Metabolism of Glycyrrhizin with Glycyrrhetic Acid Mono–Glucuronide by Mixed Eubacterium sp. GLH and Ruminococcus sp. PO1–3*, Biol. Pharm. Bull., vol. 23, No. 2, pp. 149–154 (2000).

De Roos, Nicole M., et al., *Effects of probiotic bacteria on diarrhea, lipid metabolism, and carcinogenesis: a review of papers published between 1988 and 1998*, Am. J. Clin. Nutr., vol. 71, pp. 405–411 (2000).

Jin, L.Z., et al., *Digestive and Bacterial Enzyme Activities in Broilers Fed Diets Supplemented with Lactobacillus Cultures*, Poultry Science, vol. 79, No. 6, pp. 886–891 (2000).

Klaenhammer, Todd R., *Functional Activities of Lactobacillus Probiotics: Genetic Mandate*, Int. Dairy Journal, vol. 8, pp. 497–505 (1998).

(List continued on next page.)

Primary Examiner—Rebecca E. Prouty
Assistant Examiner—David J Steadman
(74) Attorney, Agent, or Firm—Myers Bigel Sibley & Sajovec

(57) ABSTRACT

The present invention provides isolated β-Glucuronidase (GUS) having activity at acidic pH and nucleic acids encoding the same. The nucleic acids may be isolated from any suitable species, and in a preferable embodiment are isolated from *Lactobacillus gasseri*.

17 Claims, 6 Drawing Sheets

OTHER PUBLICATIONS

Kleeman, E.G., et al., *Adherence of Lactobacillus Species to Human Fetal Intestinal Cells*, J. Dairy Sci., vol. 65, No. 11, pp. 2063–2069 (1982).

McBain, A. J., et al., *Ecological and physiological studies on large intestinal bacteria in relation to production of hydrolytic and reductive enzymes involved in formation of genotoxic metabolites*, J. Med. Microbiol., vol. 47, pp. 407–416 (1998).

McConnell, M.A., et al., *A note on lactobacilli and α–glucuronidase activity in the intestinal contents of mice*, Journal of Applied Bacteriology, vol. 74, pp. 649–651 (1993).

Pham, P.L., et al., *Production of Exopolysaccharide by Lactobacillus rhamnosus R and Analysis of Its Enzymatic Degradation during Prolonged Fermentation*, Applied and Environmental Microbiology, vol. 66, No. 6, pp. 2302–2310 (Jun. 2000).

Wilson, Kate J., et al., *The Escherichia coli gus Operon: Induction and Expression of the gus Operon in E. coli and the Occurrence and Use of GUS in Other Bacteria, GUS Protocols: Using the GUS Gene as a Reporter of Gene Expression*, pp. 7–22 (1992).

pH 3.0    pH 7.5

SEQUENCE LISTING

<160> NUMBER OF SEQ ID NOS: 14

<210> SEQ ID NO 1
<211> LENGTH: 2150
<212> TYPE: DNA
<213> ORGANISM: Lactobacillus gasseri
<220> FEATURE:
<221> NAME/KEY: CDS
<222> LOCATION: (153)..(1946)

<400> SEQUENCE: 1

```
tcctttctta attattctct ataaataaaa taaactgtga cgcgaggtta cagtcaaggg      60
atttaattta ttaaaccatt ttcaaatcta tttactctcc ccaagcgtaa aatatagata    120
agagaaaaca ttactagaaa ggaaaatcat ct atg gaa tct gca cta tat cca     173
                                   Met Glu Ser Ala Leu Tyr Pro
                                    1               5 att caa aat aaa tat cgg ttt aac act tta atg aat ggc act tgg caa     221
Ile Gln Asn Lys Tyr Arg Phe Asn Thr Leu Met Asn Gly Thr Trp Gln
         10                  15                  20 ttt gaa act gat cct aac tct gtt ggt ctt gac gag gga tgg aat aaa     269
Phe Glu Thr Asp Pro Asn Ser Val Gly Leu Asp Glu Gly Trp Asn Lys
     25                  30                  35 gag ttg cct gat cct gaa gaa atg cct gta cca ggt acg ttt gca gaa     317
Glu Leu Pro Asp Pro Glu Glu Met Pro Val Pro Gly Thr Phe Ala Glu
 40                  45                  50                  55 tta act act aag cga gac cgt aaa tac tat act gga gac ttt tgg tat     365
Leu Thr Thr Lys Arg Asp Arg Lys Tyr Tyr Thr Gly Asp Phe Trp Tyr
                 60                  65                  70 caa aaa gac ttc ttt att cct tca ttt cta aag aag aaa gaa ctt tat     413
Gln Lys Asp Phe Phe Ile Pro Ser Phe Leu Lys Lys Lys Glu Leu Tyr
             75                  80                  85 atc cgt ttt ggt tcg gtt act cat cgc gca aaa gta ttt att aat gga     461
Ile Arg Phe Gly Ser Val Thr His Arg Ala Lys Val Phe Ile Asn Gly
         90                  95                 100 cat gaa gtc ggt caa cat gaa ggt ggt ttt tta cca ttt caa gta aaa     509
His Glu Val Gly Gln His Glu Gly Gly Phe Leu Pro Phe Gln Val Lys
    105                 110                 115 att tca aat tat att aat tac gac caa act aat cgt gta act gtt tta     557
Ile Ser Asn Tyr Ile Asn Tyr Asp Gln Thr Asn Arg Val Thr Val Leu
120                 125                 130                 135 gtc aat aac gaa tta tct gaa aaa gct att cct tgc ggc acc gaa gaa     605
Val Asn Asn Glu Leu Ser Glu Lys Ala Ile Pro Cys Gly Thr Glu Glu
                140                 145                 150 atc tta gat aac ggt caa aaa ctt gct caa cct tat ttt gat ttc ttc     653
Ile Leu Asp Asn Gly Gln Lys Leu Ala Gln Pro Tyr Phe Asp Phe Phe
            155                 160                 165 aat tat tct ggc att atg cgg aat gtc tgg ctc tta gca ctt cct caa     701
Asn Tyr Ser Gly Ile Met Arg Asn Val Trp Leu Leu Ala Leu Pro Gln
        170                 175                 180 agc caa atc act aat ttt aaa cta aat tat caa tta gca aat aat aag     749
Ser Gln Ile Thr Asn Phe Lys Leu Asn Tyr Gln Leu Ala Asn Asn Lys
    185                 190                 195 gca aca att acc tac aat atc gag gca aat aat aat gct gaa ttt aaa     797
Ala Thr Ile Thr Tyr Asn Ile Glu Ala Asn Asn Asn Ala Glu Phe Lys
200                 205                 210                 215
```

-continued

| | |
|---|---|
| gta aca ctt ttc gat aat caa aaa gaa gta gcg tgt gct act tct aaa<br>Val Thr Leu Phe Asp Asn Gln Lys Glu Val Ala Cys Ala Thr Ser Lys<br>220               225              230 | 845 |
| aat act agt agt tta aca att aag aat ccg cac ctt tgg agt cca aac<br>Asn Thr Ser Ser Leu Thr Ile Lys Asn Pro His Leu Trp Ser Pro Asn<br>        235               240              245 | 893 |
| gat ccg tat tca tac aaa ata aag att gaa atg ctc gaa gac gga aaa<br>Asp Pro Tyr Ser Tyr Lys Ile Lys Ile Glu Met Leu Glu Asp Gly Lys<br>            250               255              260 | 941 |
| aca gtt gac gaa tac aca gat aaa att ggt atc cgc aca gtt aaa att<br>Thr Val Asp Glu Tyr Thr Asp Lys Ile Gly Ile Arg Thr Val Lys Ile<br>265               270              275 | 989 |
| gtg aat gat aaa atc ttg ctc aat aat cac cca att tat tta aaa ggc<br>Val Asn Asp Lys Ile Leu Leu Asn Asn His Pro Ile Tyr Leu Lys Gly<br>280               285              290              295 | 1037 |
| ttt ggc aag cac gaa gat ttt aat gtt tta ggc aaa gca gtt aac gaa<br>Phe Gly Lys His Glu Asp Phe Asn Val Leu Gly Lys Ala Val Asn Glu<br>               300              305              310 | 1085 |
| agc att atc aaa cgc gac tac gaa tgc atg aaa tgg att ggc gct aac<br>Ser Ile Ile Lys Arg Asp Tyr Glu Cys Met Lys Trp Ile Gly Ala Asn<br>        315               320              325 | 1133 |
| tgt ttt aga agc agt cac tat cct tac gcc gaa gaa tgg tat caa tat<br>Cys Phe Arg Ser Ser His Tyr Pro Tyr Ala Glu Glu Trp Tyr Gln Tyr<br>            330               335              340 | 1181 |
| gcc gat aaa tat ggc ttt tta att att gat gaa gta ccc gct gtt ggt<br>Ala Asp Lys Tyr Gly Phe Leu Ile Ile Asp Glu Val Pro Ala Val Gly<br>345               350              355 | 1229 |
| ctt aat cgt tca ata act aac ttt ctt aat gta act aat tct aat cag<br>Leu Asn Arg Ser Ile Thr Asn Phe Leu Asn Val Thr Asn Ser Asn Gln<br>360               365              370              375 | 1277 |
| tcg cac ttt ttt gct tcg aaa act gtg cct gaa tta aaa aag gtc cat<br>Ser His Phe Phe Ala Ser Lys Thr Val Pro Glu Leu Lys Lys Val His<br>               380              385              390 | 1325 |
| gaa caa gaa ata aaa gaa atg atc gat cgc gac cag cgt cac cct tca<br>Glu Gln Glu Ile Lys Glu Met Ile Asp Arg Asp Gln Arg His Pro Ser<br>        395               400              405 | 1373 |
| gtg att gcc tgg agt tta ttc aat gaa cca gaa tca act act caa gaa<br>Val Ile Ala Trp Ser Leu Phe Asn Glu Pro Glu Ser Thr Thr Gln Glu<br>            410               415              420 | 1421 |
| tcc tat gac tat ttc aaa gat att ttt gcc ttt gcg aga aaa ttg gat<br>Ser Tyr Asp Tyr Phe Lys Asp Ile Phe Ala Phe Ala Arg Lys Leu Asp<br>425               430              435 | 1469 |
| cca caa aat cgt cct tat act gga act tta gtt atg ggt agc ggt cca<br>Pro Gln Asn Arg Pro Tyr Thr Gly Thr Leu Val Met Gly Ser Gly Pro<br>440               445              450              455 | 1517 |
| aaa gtg gat aag ctt cac cca ctt tgt gac ttt gtc tgc tta aac cgt<br>Lys Val Asp Lys Leu His Pro Leu Cys Asp Phe Val Cys Leu Asn Arg<br>               460              465              470 | 1565 |
| tat tat ggt tgg tac gtt gct ggt ggt cct gaa atc gtt aat gct aaa<br>Tyr Tyr Gly Trp Tyr Val Ala Gly Gly Pro Glu Ile Val Asn Ala Lys<br>        475               480              485 | 1613 |
| aag atg ctg gaa gat gaa cta gac ggc tgg caa aac tta aag ctt aat<br>Lys Met Leu Glu Asp Glu Leu Asp Gly Trp Gln Asn Leu Lys Leu Asn<br>            490               495              500 | 1661 |
| aaa cca ttt gtc ttt act gag ttt ggc gct gat aca tta tct tct tct<br>Lys Pro Phe Val Phe Thr Glu Phe Gly Ala Asp Thr Leu Ser Ser Ser<br>505               510              515 | 1709 |
| cat cgc ctt cca gat gaa atg tgg agc caa gaa tat caa aat gaa tat<br>His Arg Leu Pro Asp Glu Met Trp Ser Gln Glu Tyr Gln Asn Glu Tyr<br>520               525              530              535 | 1757 |

```
tat caa atg tat ttt gat ata ttt aag aaa tat cca ttt att tgt ggc      1805
Tyr Gln Met Tyr Phe Asp Ile Phe Lys Lys Tyr Pro Phe Ile Cys Gly
            540                 545                 550 gaa tta gtt tgg aac ttt gct gac ttt aag acg agt gaa gga atc atg      1853
Glu Leu Val Trp Asn Phe Ala Asp Phe Lys Thr Ser Glu Gly Ile Met
        555                 560                 565 cgt gtt ggt ggt aac gat aaa gga att ttt act cgc gat cgt gaa cct      1901
Arg Val Gly Gly Asn Asp Lys Gly Ile Phe Thr Arg Asp Arg Glu Pro
    570                 575                 580 aaa gat att gcc ttt acc ttg aaa aag aga tgg caa caa tta aat          1946
Lys Asp Ile Ala Phe Thr Leu Lys Lys Arg Trp Gln Gln Leu Asn
585                 590                 595 taatatttta gttttacaa ataatcgtgc tcaattaaaa ataatcgata tcattttagt     2006
tcatttgata tcgattattt gattatgggc gcgattttt attgattttg ataataattt    2066
ctaactaaga aatgtttcat taatttatga aactaatatc ttgtttctta aacaaatcat   2126
atacaactaa gtctgatgaa tcca                                          2150

<210> SEQ ID NO 2
<211> LENGTH: 598
<212> TYPE: PRT
<213> ORGANISM: Lactobacillus gasseri

<400> SEQUENCE: 2

Met Glu Ser Ala Leu Tyr Pro Ile Gln Asn Lys Tyr Arg Phe Asn Thr
1               5                   10                  15

Leu Met Asn Gly Thr Trp Gln Phe Glu Thr Asp Pro Asn Ser Val Gly
            20                  25                  30

Leu Asp Glu Gly Trp Asn Lys Glu Leu Pro Asp Pro Glu Met Pro
        35                  40                  45

Val Pro Gly Thr Phe Ala Glu Leu Thr Thr Lys Arg Asp Arg Lys Tyr
    50                  55                  60

Tyr Thr Gly Asp Phe Trp Tyr Gln Lys Asp Phe Phe Ile Pro Ser Phe
65                  70                  75                  80

Leu Lys Lys Lys Glu Leu Tyr Ile Arg Phe Gly Ser Val Thr His Arg
                85                  90                  95

Ala Lys Val Phe Ile Asn Gly His Glu Val Gly Gln His Glu Gly Gly
            100                 105                 110

Phe Leu Pro Phe Gln Val Lys Ile Ser Asn Tyr Ile Asn Tyr Asp Gln
        115                 120                 125

Thr Asn Arg Val Thr Val Leu Val Asn Asn Glu Leu Ser Glu Lys Ala
    130                 135                 140

Ile Pro Cys Gly Thr Glu Glu Ile Leu Asp Asn Gly Gln Lys Leu Ala
145                 150                 155                 160

Gln Pro Tyr Phe Asp Phe Phe Asn Tyr Ser Gly Ile Met Arg Asn Val
                165                 170                 175

Trp Leu Leu Ala Leu Pro Gln Ser Gln Ile Thr Asn Phe Lys Leu Asn
            180                 185                 190

Tyr Gln Leu Ala Asn Asn Lys Ala Thr Ile Thr Tyr Asn Ile Glu Ala
        195                 200                 205

Asn Asn Asn Ala Glu Phe Lys Val Thr Leu Phe Asp Asn Gln Lys Glu
    210                 215                 220

Val Ala Cys Ala Thr Ser Lys Asn Thr Ser Ser Leu Thr Ile Lys Asn
225                 230                 235                 240

Pro His Leu Trp Ser Pro Asn Asp Pro Tyr Ser Tyr Lys Ile Lys Ile
```

```
                    245                 250                 255
Glu Met Leu Glu Asp Gly Lys Thr Val Asp Glu Tyr Thr Asp Lys Ile
                260                 265                 270

Gly Ile Arg Thr Val Lys Ile Val Asn Asp Lys Ile Leu Leu Asn Asn
            275                 280                 285

His Pro Ile Tyr Leu Lys Gly Phe Gly Lys His Glu Asp Phe Asn Val
        290                 295                 300

Leu Gly Lys Ala Val Asn Glu Ser Ile Ile Lys Arg Asp Tyr Glu Cys
305                 310                 315                 320

Met Lys Trp Ile Gly Ala Asn Cys Phe Arg Ser Ser His Tyr Pro Tyr
                325                 330                 335

Ala Glu Glu Trp Tyr Gln Tyr Ala Asp Lys Tyr Gly Phe Leu Ile Ile
            340                 345                 350

Asp Glu Val Pro Ala Val Gly Leu Asn Arg Ser Ile Thr Asn Phe Leu
        355                 360                 365

Asn Val Thr Asn Ser Asn Gln Ser His Phe Phe Ala Ser Lys Thr Val
    370                 375                 380

Pro Glu Leu Lys Lys Val His Glu Gln Glu Ile Lys Glu Met Ile Asp
385                 390                 395                 400

Arg Asp Gln Arg His Pro Ser Val Ile Ala Trp Ser Leu Phe Asn Glu
                405                 410                 415

Pro Glu Ser Thr Thr Gln Glu Ser Tyr Asp Tyr Phe Lys Asp Ile Phe
            420                 425                 430

Ala Phe Ala Arg Lys Leu Asp Pro Gln Asn Arg Pro Tyr Thr Gly Thr
        435                 440                 445

Leu Val Met Gly Ser Gly Pro Lys Val Asp Lys Leu His Pro Leu Cys
    450                 455                 460

Asp Phe Val Cys Leu Asn Arg Tyr Tyr Gly Trp Tyr Val Ala Gly Gly
465                 470                 475                 480

Pro Glu Ile Val Asn Ala Lys Lys Met Leu Glu Asp Glu Leu Asp Gly
                485                 490                 495

Trp Gln Asn Leu Lys Leu Asn Lys Pro Phe Val Phe Thr Glu Phe Gly
            500                 505                 510

Ala Asp Thr Leu Ser Ser Ser His Arg Leu Pro Asp Glu Met Trp Ser
        515                 520                 525

Gln Glu Tyr Gln Asn Glu Tyr Tyr Gln Met Tyr Phe Asp Ile Phe Lys
    530                 535                 540

Lys Tyr Pro Phe Ile Cys Gly Glu Leu Val Trp Asn Phe Ala Asp Phe
545                 550                 555                 560

Lys Thr Ser Glu Gly Ile Met Arg Val Gly Asn Asp Lys Gly Ile
                565                 570                 575

Phe Thr Arg Asp Arg Glu Pro Lys Asp Ile Ala Phe Thr Leu Lys Lys
            580                 585                 590

Arg Trp Gln Gln Leu Asn
        595

<210> SEQ ID NO 3
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic Oligonucleotide Primer.

<400> SEQUENCE: 3
```

```
agtcagatct acagctccag atcgattcac                                    30

<210> SEQ ID NO 4
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic Oligonucleotide Primer.

<400> SEQUENCE: 4
agtcgctagc ttacgaactg gcacagatgg                                    30

<210> SEQ ID NO 5
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: Synthetic Oligonucleotide Primer.

<400> SEQUENCE: 5
agtcagatct ttaatgcgcc gctacagg                                      28

<210> SEQ ID NO 6
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: Synthetic Oligonucleotide Primer.

<400> SEQUENCE: 6
agtcgctagc aatgcagcag ctggcacgac agg                                33

<210> SEQ ID NO 7
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic Oligonucleotide Primer.

<400> SEQUENCE: 7
agagtcgact aatgaagctt gttttgtttc ag                                 32

<210> SEQ ID NO 8
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Synthetic Oligonucleotide Primer.

<400> SEQUENCE: 8
actgaattct tctttagtta atggctcag                                     29

<210> SEQ ID NO 9
<211> LENGTH: 29
<212> TYPE: DNA
<213> ORGANISM: Artificial Sequence
<220> FEATURE:
```

```
<221> NAME/KEY: misc_feature
<222> LOCATION: (1)..(29)
<223> OTHER INFORMATION: Synthetic Oligonucleotide Primer.

<400> SEQUENCE: 9
gtcgaattct actagaaagg aaaatcatc                                      29

<210> SEQ ID NO 10
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Synthetic Oligonucleotide Primer.

<400> SEQUENCE: 10
tgctctagat aattgagcac gattatttg                                      29

<210> SEQ ID NO 11
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic Oligonucleotide Primer.

<400> SEQUENCE: 11
agtccatgga atctgcacta tatccaattc                                     30

<210> SEQ ID NO 12
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic Oligonucleotide Primer.

<400> SEQUENCE: 12
actggaattc taattgagca cgattatttg                                     30

<210> SEQ ID NO 13
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic Oligonucleotide Primer - GUS-1F

<400> SEQUENCE: 13
acagttgcga atacacagat                                                20

<210> SEQ ID NO 14
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic Oligonucleotide Primer - GUS-1R.

<400> SEQUENCE: 14
aggcgatgag aagaagataa tg                                             22
```

POLYNUCLEOTIDE ENCODING A *LACTOBACILLUS GASSERI* BETA-GLUCURONIDASE POLYPEPTIDE

RELATED APPLICATIONS

This application claims the benefit of U.S. Provisional Application Ser. No. 60/206,372, filed May 23, 2000, the disclosure of which is incorporated by reference herein in its entirety.

FIELD OF THE INVENTION

The present invention concerns β-glucuronidase (GUS) proteins, DNA encoding the same, and methods of use thereof.

BACKGROUND OF THE INVENTION

β-Glucuronidase protein (GUS) and the gene encoding this protein (gusA) are widely used as reporter genes and proteins in molecular biology. Bacterial β-glucuronidase activity has been considered for many years to be almost unique to *Escherichia coli* and closely related Enterobacteriaceae (Wilson et al. (1992) The *Escherichia coli* gus operon: induction and expression of the gus operon in *E. coli* and the occurrence and use of GUS in other bacteria. In. S. R. Gallagher (ed.), GUS Protocols: using the GUS gene as a reporter of gene expression. Academic Press, San Diego, Calif.). However, evidence has slowly been accumulating to indicate that β-glucuronidase activity can also be found in a limited number of other bacteria, particularly gram-positive inhabitants of the GI tract (Akao (2000) *Biol. Pharm. Bull.* 23:149–154; Akao (2000) *Biol. Pharm. Bull.* 22:80–82; Hawkesworth et al. (1971) *J. Med. Microbiol.* 4:451–459; McBain and Macfarlane (1998) *J. Med. Microbiol.* 47:407–415). The gusA gene can also be found in Shigella species but activity is absent in many of the common, agriculturally-important bacterial species, such as Rhizobium, Agrobacterium, and Pseudomonas (GUS Protocols, 7–17 (S. Gallagher Ed. 1992)).

*Lactobacillus gasseri* ADH is a human intestinal isolate that was identified by its ability to adhere to intestinal epithelial cells (Kleeman and Klaenhammer (1982) *J. Dairy Sci.* 65:2063–2069). *L. gasseri* is one of a number of indigenous lactobacilli that are commonly associated with the microflora of a healthy human GI tract (Molin et al. (1993) *J. Appl. Bacteriol.* 74:314–323; Song et al. (2000) *FEMS Microbiol. Lett.* 187:167–173). A number of these lactobacilli are currently under investigation to determine the mechanistic basis of a variety of proposed probiotic activities (Klaenhammer (1998) *Int. Dairy J.* 8:497–506). It remains an important objective to characterize the physiological and enzymatic activities of this group of organisms and ultimately to identify the genetic factors responsible for those activities. Studies with various Lactobacillus species, including *L. gasseri*, have consistently shown their ability to reduce the amount of fecal β-glucuronidase activity and lower the occurrence of cancer indicators present in the GI tract (de Roos and Katan (2000) *Am. J. Clin. Nutr.* 71:405–411; Jin et al. (2000) *Poult. Sci* 79:886–891; Ling et al. (1992) *Ann. Nutr. Metab.* 36:162–166; McConnell and Tannock (1993) *J. Appl. Bacteriol.* 74:649–651; Pedrosa et al. (1995) *Am. J Clin. Nutr.* 61:353–359). The mechanisms by which lactobacilli lower the amount of β-glucuronidase activity in the gut remain unknown but may be the reflection of a variety of activities including, but not limited to, the exclusion or antagonism of typically β-glucuronidase-positive enterobacteria. Because lactobacilli colonize the proximal region of the small intestine, it is reasonable to expect them to be frequently exposed to β-D-glucuronides excreted via bile into the GI tract. Indeed, their frequent exposure to bile is reflected in the common occurrence of conjugated bile acid hydrolysis among different species (Christiaens et al. (1992) *Appl. Environ. Microbiol.* 58:3792–3798; Elkins and Savage (1998) *J. Bacteriol.* 180:4344–4349). Lactobacilli themselves have not traditionally been associated with β-glucuronidase activity, however, and there have been, to date, only two reports of β-glucuronidase-like activity in lactobacilli (McConnell and Tannock (1993) *J. Appl. Bacteriol.* 74:649–651; Pham et al (2000) *Appl. Environ. Microbiol.* 66:2302–2310). It has been unclear, however, whether this β-glucuronidase activity was the result of a true β-glucuronidase enzyme or reflected the activity of some other enzyme.

A disadvantage of currently available GUS proteins is that they have limited activity in acidic pH environments. Since acidic pH environments characterize a variety of industrial fermentation processes in which current GUS proteins cannot be be effectively used, it would be extremely useful to have new GUS proteins that operate at an acidic pH.

SUMMARY OF THE INVENTION

Accordingly, the invention provides isolated polynucleotides encoding the protein beta-glucuronidase (GUS), and which are preferably operable at a pH of less than 7 (e.g., are operable at a pH of 4 or 5). The polynucleotide sequence may be selected from the group consisting of:

(a) DNA having the nucleotide sequence given herein as SEQ ID NO:1 (which encodes the protein having the amino acid sequence given herein as SEQ ID NO:2);

(b) polynucleotides (e.g., cDNAs) that hybridize to DNA of (a) above (e.g., under stringent conditions) and which encode the protein β-glucuronidase (GUS); and (c) polynucleotides that differ from the DNA of (a) or (b) above due to the degeneracy of the genetic code, and which encode the protein encoded by a DNA of (a) or (b) above.

The present invention further provides vector (e.g., an expression vector) containing at least a fragment of any of the claimed polynucleotide sequences. In yet another aspect, the expression vector containing the polynucleotide sequence is contained within a host cell.

The invention further provides a protein or fragment thereof encoded by a polynucleotide as given above (e.g., the protein provided herein as SEQ ID NO: 2). Such proteins may be isolated and/or purified in accordance with known techniques.

The invention also provides a method for producing a polypeptide comprising the amino acid sequence of SEQ ID NO:2, or a fragment thereof, the method comprising the steps of: a) culturing the host cell containing an expression vector containing at least a fragment of the polynucleotide sequence encoding GUS under conditions suitable for the expression of the polypeptide; and b) recovering the polypeptide from the host cell culture.

The invention also provides an antibody (e.g., a polyclonal antibody, a monoclonal antibody) which specifically binds to a protein as given above.

DETAILED DESCRIPTION OF THE PREFERRED EMBODIMENTS

Figure 1:
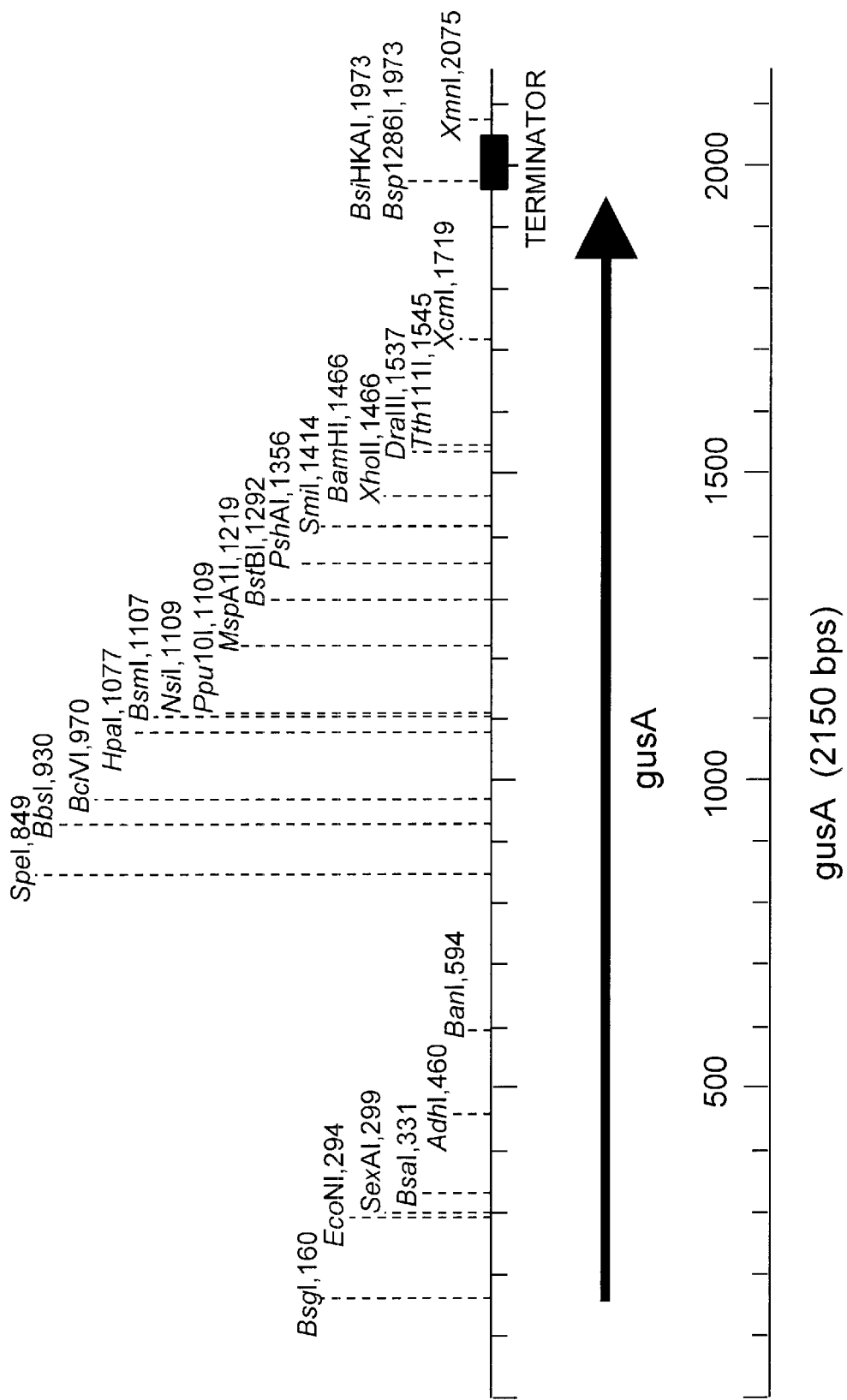
FIG. 1 depicts the gusA locus of 2150 bp which includes the open reading frame (filled arrow), the promoter (5' of arrow), and terminator sequence (filled box). Restriction enzyme cleavage sites are indicated above the line.

The present invention will now be described more fully hereinafter with reference to the accompanying figures, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 C.F.R §1.822 and established usage. See, e.g., PatentIn User Manual, 99–102 (November 1990) (U.S. Patent and Trademark Office).

1. Definitions

The GUS protein, as used herein, refers to the amino acid sequence of substantially purified GUS obtained from any species and is substantially homologous to the proteins described herein. GUS protein as described herein may be obtained from the genus Lactobacillus and preferably from *L. gasseri* ADH. GUS proteins as described herein preferably have maximum activity at an acidic pH, e.g., at a pH less than 7 or 6, and may have a maximum activity at a pH of from 3 to 5 or 6.

An "allele" or "allelic sequence," as used herein, is an alternative form of the genes encoding GUS. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

"Antibody" as used herein refers to intact molecules as well as fragments thereof, such as Fa, F(ab')2, and Fc, and chimeras thereof, which are capable of binding the epitopic determinant. Antibodies that bind GUS polypeptides can be prepared using intact GUS or fragments containing small peptides of interest as the immunizing antigen.

"Homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

The term "hybridization", as used herein, refers to any process by which a strand of nucleic acid binds with a complementary strand through base pairing. The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

By "nucleic acid' or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925

(1993) and references therein; Letsinger, *J. Org. Chem.,* 35:3800 (1970); Sprinzl, et al., *Eur. J. Biochem.,* 81:579 (1977); Letsinger, et al., *Nucl. Acids Res.,* 14:3487 (1986); Sawai, et al., *Chem. Lett.,* 805 (1984), Letsinger, et al., *J. Am. Chem. Soc.,* 110:4470 (1988); and Pauwels, et al., *Chemica Scripta,* 26:141 (1986)), phosphorothioate (Mag, et al., *Nucleic Acids Res.,* 19:1437 (1991); and U.S. Pat. No. 5,644,048), phosphorodithioate (Briu, et al., *J. Am. Chem. Soc.,* 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.,* 114:1895 (1992); Meier, et al., *Chem. Int. Ed. Engl.,* 31:1008 (1992); Nielsen, *Nature,* 365:566 (1993); Carlsson, et al., *Nature,* 380:207 (1996), all of which are incorporated by reference)). Other analog nucleic acids include those with positive backbones (Denpcy, et al., *Proc. Natl. Acad. Sci. USA,* 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English,* 30:423 (1991); Letsinger, et al., *J. Am. Chem. Soc.,* 110:4470 (1988); Letsinger, et al., Nucleoside & Nucleotide, 13:1597 (1994); Chapters 2 and 3, ASC Symposium Series 580, "Carbohydrate Modifications in Antisense Research," Ed. Y. S. Sanghui and P. Dan Cook; Mesmaeker, et al., *Bioorganic & Medicinal Chem. Lett.,* 4:395 (1994); Jeffs, et al., *J. Biomolecular NMR,* 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research," Ed. Y. S. Sanghui and P. Dan Cook. Nucleic acids containing one or more carbocyclic sugars are also included within the definition of nucleic acids (see Jenkins, et al., *Chem. Soc. Rev.,* (1995) pp. 169–176). Several nucleic acid analogs are described in Rawls, *C & E News,* Jun. 2, 1997, page 35. These modifications of the ribose-phosphate backbone may be done to facilitate the addition of additional moieties such as labels, or to increase the stability and half-life of such molecules in physiological environments. In addition, mixtures of naturally-occurring nucleic acids and analogs can be made. Alternatively, mixtures of different nucleic acid analogs, and mixtures of naturally-occurring nucleic acids and analogs may be made. The nucleic acids may be single-stranded or double-stranded, as specified, or contain portions of both double-stranded or single-stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally-occurring nucleic acids, random nucleic acids, or "biased" random nucleic acids. For example, digests of procaryotic or eukaryotic genomes may be used as is outlined above for proteins.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray.

As used herein, oligonucleotide is substantially equivalent to the terms "amplimers", "primers", "oligomers", and "probes", as commonly defined in the art.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° below the melting temperature of the probe to about 20° C. to 25°. below the melting temperature). One or more factors may be varied to generate conditions of either low or high stringency different from, but equivalent to, the above listed conditions.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably-transformed cells in which the inserted DNA is capable of replication either as an autonomously replicating plasmid or as part of the host chromosome. They also include cells which transiently express the inserted DNA or RNA for limited periods of time.

2. β-Glucuronidase (GUS) Coding Sequences

Polynucleotides of the present invention include those coding for proteins homologous to, and having essentially the same biological properties as, the proteins disclosed herein, and particularly the DNA disclosed herein as SEQ ID NO:1 and encoding the protein GUS given herein SEQ ID NO:2. This definition is intended to encompass natural allelic sequences thereof. Thus, isolated DNA or cloned genes of the present invention can be of any isolate of *Lactobacillus gasseri*, such as *Lactobacillus gasseri* ADHn. Thus, polynucleotides that hybridize to DNA disclosed herein as SEQ ID NO:1 (or fragments or derivatives thereof which serve as hybridization probes as discussed below) and which code on expression for a protein of the present invention (e.g., a protein according to SEQ ID NO:2) are also an aspect of the invention. Conditions which will permit other polynucleotides that code on expression for a protein of the present invention to hybridize to the DNA of SEQ ID NO:1 disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively) to DNA of SEQ ID NO:1 disclosed herein in a standard hybridization assay. See, e.g., J. Sambrook et al.,

*Molecular Cloning, A Laboratory Manual* (2d Ed. 1989) (Cold Spring Harbor Laboratory). In general, sequences which code for proteins of the present invention and which hybridize to the DNA of SEQ ID NO:1 disclosed herein will be at least 60% homologous, 70% homologous, 80% homologous, or even 90% homologous or more with SEQ ID NO:1. Further, polynucleotides that code for proteins of the present invention, or polynucleotides that hybridize to that as SEQ ID NO:1, but which differ in codon sequence from SEQ ID NO:1 due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

Although nucleotide sequences which encode GUS and its variants are preferably capable of hybridizing to the nucleotide sequence of the naturally-occurring gusA under appropriately-selected conditions of stringency, it may be advantageous to produce nucleotide sequences encoding GUS or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially-altering the nucleotide sequence encoding GUS and its derivatives without altering the encoded amino acid sequences include the production of RNA transcripts having more desirable properties, such as a greater half-life, than transcripts produced from the naturally-occurring sequence.

In one embodiment of the invention, gusA nucleic acids (defined as polynucleotides encoding GUS proteins or fragments thereof), or GUS proteins (as defined above) are initially-identified by substantial nucleic acid and/or amino acid sequence identity or similarity to the sequence(s) provided herein. In a preferred embodiment, gusA nucleic acids or GUS proteins have sequence identity or similarity to the sequences provided herein as described below and one or more of the GUS protein bioactivities as further described herein. Such sequence identity or similarity can be based upon the overall nucleic acid or amino acid sequence.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48,443 (1970), by the search for similarity method of Pearson & Lipman, *Proc. Natl. Acad. Sci. USA* 85,2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," *Macromolecule Sequencing and Synthesis, Selected Methods and Applications*, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351–360 (1987); the method is similar to that described by Higgins & Sharp *CABIOS* 5, 151–153 (1989). Useful PILEUP parameters including a default gap weight of 3.00, a default gap length weight of 0.10, and weighted end gaps.

Another example of a useful algorithm is the BLAST algorithm, described in Altschul et al., *J. Mol. Biol.* 215, 403–410, (1990) and Karlin et al., *Proc. Natl. Acad. Sci. USA* 90, 5873–5787 (1993). A particularly useful BLAST program is the WU-BLAST-2 program which was obtained from Altschul et al., *Methods in Enzymology*, 266,460–480 (1996). WU-BLAST-2 uses several search parameters, most of which are set to the default values. The adjustable parameters are set with the following values: overlap span= 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. *Nucleic Acids Res.* 25, 3389–3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence in SEQ ID NO:1, it is understood that in one embodiment, the percentage of sequence identity will be determined based on the number of identical amino acids in relation to the total number of amino acids. Thus, for example, sequence identity of sequences shorter than that shown in the Figure, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

The invention also encompasses production of DNA sequences, or fragments thereof, which encode GUS and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding GUS or any fragment thereof.

Knowledge of the nucleotide sequence as disclosed herein in SEQ ID NO:1 can be used to generate hybridization probes which specifically bind to the DNA of the present invention or to mRNA to determine the presence of amplification or overexpression of the proteins of the present invention.

3. Expression of Nucleic Acids Encoding GUS

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

Methods for DNA sequencing which are well known and generally available in the art may be used to practice any of the embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequence encoding GUS may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) *PCR Methods Applic.* 2, 318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably-associated when they are functionally-related to each other. For example, a promoter is operably-linked to a coding sequence if it controls the transcription of the sequence; a ribosome binding site is operably-linked to a coding sequence if it is positioned so as to permit translation. Generally, operably-linked means contiguous and, in the case of leader sequences, contiguous and in reading phase.

Transformed host cells are cells which have been transformed or transfected with vectors containing DNA coding for proteins of the present invention and need not express protein.

Suitable host cells include bacterial cells, yeast cells, or higher eukaryotic organism cells. Bacterial cells that may be employed as host cells include lactic acid bacteria, such as Lactobacillus and Lactococcus bacteria. Higher eukaryotic cells include plants (e.g., vascular plants such as monocots and dicots) and plant cells and established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. See Bolivar et al., *Gene* 2, 95 (1977). Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983). The promoter and Shine-Dalgarno sequence (for prokaryotic host expression) are operably-linked to the DNA of the present invention, i.e., they are positioned so as to promote transcription of the messenger RNA from the DNA.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21

(1983). While these are commonly used, other microbial promoters are suitable. Details concerning nucleotide sequences of many have been published, enabling a skilled worker to operably-ligate them to DNA encoding the protein in plasmid or viral vectors (Siebenlist et al., *Cell* 20, 269 (1980). The promoter and Shine-Dalgarno sequence (for prokaryotic host expression) are operably-linked to the DNA encoding the desired protein, i.e., they are positioned so as to promote transcription of the protein messenger RNA from the DNA.

Eukaryotic microbes such as yeast cultures may be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or anautonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977). The presence of the trp1 lesion in the yeast host cell genome then provides an effective environment for detecting transformation by growth in the absence of tryptophan.

Suitable promoting sequences in yeast vectors include the promoters for metallothionein, 3-phospho-glycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Plants can be transformed according to the present invention using any suitable method known in the art. Intact plants, plant tissue, isolated cells, protoplasts, callus tissue, and the like may be used for transformation depending on the plant species and the method employed. .

Exemplary transformation methods include biological methods using viruses (RNA and DNA viruses) and Agrobacterium (See, e.g., Hooykaas, *Plant Mol. Biol.* 13, 327 (1989); Smith et al., *Crop Science* 35, 301 (1995); Chilton, *Proc. Natl. Acad. Sci. USA* 90, 3119 (1993); Mollony et al., *Monograph Theor. Appl. Genet NY* 19, 148 (1993); Ishida et al., *Nature Biotechnol.* 14, 745 (1996); and Komari et al., *The Plant Journal* 10, 165 (1996)), physicochemical methods such as electroporation, polyethylene glycol, ballistic bombardment, microinjection, and the like. In one form of direct transformation, the vector is microinjected directly into plant cells by use of micropipettes to mechanically transfer the recombinant DNA (Crossway, *Mol. Gen. Genetics* (1985) 202:179–185). In another protocol, the genetic material is transferred into the plant cell using polyethylene glycol (Krens, et al. *Nature* (1982) 296:72–74). In still another method, protoplasts are fused with minicells, cells, lysosomes, or other fusible lipid-surfaced bodies that contain the nucleotide sequence to be transferred to the plant (Fraley, et al., *Proc. Natl. Acad. Sci. USA* (1982) 79:1859–1863). DNA may also be introduced into the plant cells by electroporation (Fromm et al., *Proc. Natl. Acad. Sci. USA* (1985) 82:5824). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide and regenerate. One advantage of electroporation is that large pieces of DNA, including artificial chromosomes, can be transformed by this method.

Two exemplary classes of recombinant Ti and Ri plasmid vector systems are commonly used in the art. In one class, called "cointegrate," the shuttle vector containing the gene of interest is inserted by genetic recombination into a non-oncogenic Ti plasmid that contains both the cis-acting and trans-acting elements required for plant transformation as, for example, in the PMLJ1 shuttle vector of DeBlock et al., *EMBO J* (1984) 3:1681–1689, and the non-oncogenic Ti plasmid pGV2850 described by Zambryski et al., *EMBO J* (1983) 2:2143–2150. In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* (1984) 12:8711–8721, and the non-oncogenic Ti plasmid PAL4404 described by Hoekma, et al., *Nature* (1983) 303:179–180.

Plant cells may be transformed with Agrobacteria by any means known in the art, e.g., by co-cultivation with cultured isolated protoplasts, or transformation of intact cells or tissues. The first requires an established culture system that allows for culturing protoplasts and subsequent plant regeneration from cultured protoplasts. Identification of transformed cells or plants is generally accomplished by including a selectable marker in the transforming vector, or by obtaining evidence of successful bacterial infection.

In plants stably-transformed by Agrobacteria-mediated transformation, the nucleotide sequence of interest is incorporated into the plant genome, typically flanked by at least one T-DNA border sequence. Preferably, the nucleotide sequence of interest is flanked by two T-DNA border sequences.

Plant cells which have been transformed by any method known in the art can also be regenerated to produce intact plants using known techniques.

Plant regeneration from cultured protoplasts is described in Evans et al., *Handbook of Plant Cell Cultures*, Vol. 1: (MacMilan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues, including but not limited to, all major species of sugar-cane, sugar beet, cotton, fruit trees, and legumes.

The particular conditions for transformation, selection and regeneration may be optimized by those of skill in the art. Factors that affect the efficiency of transformation include the species of plant, the tissue infected, composition of the media for tissue culture, selectable marker genes, the length of any of the above-described step, kinds of vectors, and light/dark conditions. Therefore, these and other factors may be varied to determine what is an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., Nature 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculorivus expression vector (e.g., vectors derived from *Autographa californica* MNPV, *Trichoplusia ni* MNPV, *Rachiplusia ou* MNPV, or *Galleria ou* MNPV) may be employed to make proteins useful in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

In mammalian host cells, a number of viral-based expression systems may be utilized. In cases where an adenovirus is used as an expression vector, sequences encoding GUS may be ligated into an adenovirus transcription/translation complex consisting of the late promoter and tripartite leader sequence. Insertion in a non-essential E1 or E3 region of the viral genome may be used to obtain a viable virus which is capable of expressing GUS in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Rather than using vectors which contain viral origins of replication, one can transform mammalian cells by the method of cotransformation with a selectable-marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival or transformants in culture medium that is toxic, or from which the cells cannot obtain critical nutrition without having taken up the marker protein.

In addition to their use as markers, nucleic acids of the present invention, constructs containing the same and host cells that express the encoded proteins are useful for making proteins of the present invention.

4. GUS Proteins

As noted above, the present invention provides isolated and purified GUS protein, such as Lactobacillus (or more preferably *L. gasseri*) GUS. Such proteins can be purified from host cells which express the same, in accordance with known techniques, or even manufactured synthetically.

Proteins of the present invention are useful as, among other things, standard reagents in GUS assays and as immunogens for making antibodies as described herein, and these antibodies and proteins provide a "specific binding pair." Such specific binding pairs are useful as components of a variety of immunoassays and purification techniques (e.g., for the affinity purification of GUS protein), as is known in the art.

A variety of protocols for detecting and measuring the expression of GUS, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on GUS can be used, but a competitive binding assay may be employed. These and other assays are described, among other places, in Hampton, R. et al. (1990; *Serological Methods, a Laboratory Manual*, APS Press, St Paul, Minn.) and Maddox, D. E. et al. ((1983) *J. Exp. Med.* 158:1211–1216).

A wide variety of labels and conjugation techniques are known by those skilled in the art and may be used in various nucleic acid and amino acid assays. Means for producing labeled-hybridization or PCR probes for detecting sequences related to polynucleotides encoding GUS include oligolabeling, nick translation, end-labeling or PCR amplification using a labeled nucleotide. Alternatively, the sequences encoding GUS, or any fragments thereof may be cloned into a vector for the production of an mRNA probe. Such vectors are known in the art, are commercially-available, and may be used to synthesize RNA probes in vitro by addition of an appropriate RNA polymerase such as T7, T3, or SP6 and labeled nucleotides. These procedures may be conducted using a variety of commercially-available kits (Pharmacia & Upjohn, (Kalamazoo, Mich.); Promega (Madison Wis.); and U.S. Biochemical Corp., Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding GUS may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode GUS may be designed to contain signal sequences which direct secretion of GUS through a prokaryotic or eukaryotic cell membrane. Other constructions may be used to join sequences encoding GUS to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and GUS may be used to facilitate purification. One such expression vector provides for expression of a fusion protein containing GUS and a nucleic acid encoding 6 histidine residues preceding a thioredoxin or an enterokinase cleavage site. The histidine residues facilitate purification on IMAC (immobilized metal ion affinity chromatography) as described in Porath, J. et al. ((1992), *Prot. Exp. Purif.* 3, 263–281) while the enterokinase cleavage site provides a means for purifying GUS from the fusion protein. A discussion of vectors which contain fusion proteins is provided in Kroll, D. J. et al. (1993) *DNA Cell Biol.* 12:441–453).

In addition to recombinant production, fragments of GUS may be produced by direct peptide synthesis using solid-phase techniques (Merrifield J. (1963) *J. Am. Chem. Soc.* 85, 2149–2154). Protein synthesis may be performed using manual techniques or by automation. Automated synthesis may be achieved, for example, using Applied Biosystems 431A Peptide Synthesizer (Perkin Elmer). Various fragments of GUS may be chemically-ynthesized separately and combined using chemical methods to produce the full-length molecule.

5. GUS Substrates and Assays

Assays for detecting the enzyme activity of GUS in a cell, or the extent of such activity, typically involve, first, contacting the cells or extracts of the cells containing proteins therefrom with a substrate that specifically binds to GUS enzyme as given herein (typically under conditions that permit access of the substrate to intracellular material), and then detecting the presence or absence of binding of the substrate thereto (e.g., by detecting the product of a chemical reaction on the substrate catalyzed by GUS). Again, any suitable assay format, including cell-free extracts or nondestructive methods to stain cells expressing GUS, can be employed.

Test methods for the determination of GUS activity include but are not limited to the use of fluorogenic and chromogenic chemicals, i.e. are 5-bromo-4-chloro-3-indolyl-beta-D-glucuronide (X-GlcU) and para-nitrophyenyl β-D-glucuronide (PNPG), and 4-methylumbelliferyl-β-D-glucuronide (MUG). Many types of substrates (yielding either soluble, insoluble, or fluorescent products upon enzymatic cleavage) are available for detecting beta-glucuronidase. These substrates typically contain the sugar D-glucopyranosiduronic acid attached by a glycosidic linkage to a hydroxyl group of a chromogenic, fluorogenic, or other detectible molecule. Chromogenic substrates available for detection of beta-glucuronidase are, but are not limited to, 5-bromo-4-chloro-3-indolyl-beta-D-glucuronide (X-GlcU) and para-nitrophyenyl β-D-glucuronide (PNPG), and 5-bromo-6-chloro-3-indolyl-beta-D-glucuronide (Magenta-GlcA). The chromogenic substrates themselves are not colored so that the detection of colored transformed or transfected cells or cell extracts indicates the presence of the enzyme. The chromogenic substrates have been used to detect GUS activity in transformed plant cells and tissues (Sawahel and Fukui (1995) *BioTechniques* 19, 106; Fromm et al. (1990) *Bio/Technology* 8, 833), *Saccharomyces cerevisae* (Schmitz et al. (1990) *Curr. Genet.* 17: 261) and used to detect *E. coli* contamination in food and water (Frampton and Restaino (1993) *J. Appl. Bacteriol.* 74, 223; Ogden and Watt (1991) *Lett. Appl. Microbiol.* 13, 212; U.S. Pat. No. 4,923,804).

Similarly, fluorogenic substrates available for detection of beta-glucuronidase include are, but are not limited to, 4-methylumbelliferyl-β-D-glucuronide (MUG), 6,8-difluoro-4-methylumbelliferyl β-D-glucuronide (DiFMUGlcU), resorufin-β-D-glucuronide (ReG), 4-trifluoromethylumbelliferyl β-D-glucuronic acid (TFMUG), fluorescein mono-β-D-glucuronide, fluorescein di-β-D-glucuronide (FDGlcU), 5-(pentafluorobenzoylamino)fluorescein di-β-D-glucuronide (PFB-FDGlcU), DDAO β-D-glucuronide (DDAO GlcU), and naphthol-AS-BI β-D-glucuronide. The fluorogenic substrates have been used to detect GUS activity in whole plant tissue and plant extracts expressing *E. coli* GUS (Jefferson (1988) *Plant Mol. Biol. Rep.* 5, 387; Gallagher (1992) *GUS Protocols: Using the GUS Gene as a Reporter for Gene Expression*, Academic Press, Inc., San Diego, Calif.; Martin et al. (1992) *Plant Mol. Biol. Rep.* 10, 37), in the flow cytometric assay of individual mammalian cells expressing the *E. coli* GUS gene (Lorinez et al. (1996) *Cytometry* 24, 321; Lorincz et al. (1999) *J. Biol. Chem.* 274, 657), in detecting *E. coli* contamination in food and water (U.S. Pat. Nos. 5,861,270; 5,935,799), and in detecting lysosomal enzyme release from neutrophils (Niessen et al. (1991) *Cell Signal* 3, 625). In addition there are lipophilic derivatives, such as the ImaGene Green $C_{12}$FDGlcU GUS Gene Expression Kit (Molecular Probes, Inc., OR) which will freely diffuse across the membranes of viable cultured tobacco leaf cells or protoplasts under physiological conditions (Fleming et al. (1996) *Plant J.* 10, 745).

Methods of exposing the cell or cell-free extracts to substrate include, but not limited to, tissue or cell homogenization to release intracellular material, histochemical staining of cells or tissues fixed with paraformaldehyde, vacuum infiltration of whole tissue or cells, and non-destructive exposure of whole tissue or cells by submerging tissue in substrate or spraying tissue with substrate.

Method of detecting release of chromogenic or fluorogenic molecules from substrates by GUS include, but are not limited to spectrophotometric, fluorometric, and microscopic visualization at the wavelengths appropriate for the detection of the released products.

As this *L. gasseri* ADH gusA gene product has a maximal enzyme activity at low pH (3–5), it may be used as a reporter protein for organisms that are extremely aciduric. The protein itself may be used as a protein tag and detected by antibodies or activity or may be used as a marker of transformed cells.

The *E. coli* GUS enzyme has been used in many systems including plants, animals, fungi, and bacteria. The *E. coli* and human enzymes have pH optima close to neutral and the plant enzyme has a pH optima of 5.0 (Alwen et al. (1992) *Transgenic Res.* 1:63). To overcome the pH optima overlap of GUS of mammalian origin and *E. coli* origin, researchers have had to use suboptimal pH conditions and calculations of percents of activity to determine individual activities of these enzymes (Ho and Ho (1985) *J. Urol.* 134:1227). The present invention has the advantage that it can be used as a more distinguisable marker in mammalian systems and as a reporter in extremely aciduric organisms, where reliable reporter molecules have been scarce. Furthermore, because the current invention may differ in codon usage, functional pH range, substrate specificity, temperature optimum, or resistance to chemical treatment, it may have advantages over the prior art in specific applications or target organisms. Moreover, the differences listed above would be advantageous and allow for a two, three, four or more reporter strategy where each enzyme is detected at a different pH, with a different substrate, or at a different temperature optimum.

In a preferred embodiment, the GUS proteins, nucleic acids, variants, modified proteins, cells and/or transgenics containing the gusA nucleic acids or proteins are used in screening assays. Identification of the GUS proteins provided herein permits the presence of GUS protein as a marker protein in low pH environments.

The assays described herein preferably utilize the *L. gasseri* ADH GUS protein, although proteins from other *Lactobacillus gasseri* isolates may also be used, or homologous proteins from other species that encode a GUS having activity at a low pH. These latter embodiments may be preferred in the development of reporter proteins. In some embodiments, variant or derivative GUS proteins may be used.

A variety of other reagents may be included in the assays. These include reagents like salts, neutral proteins, e.g. albumin, detergents, etc which may be used to facilitate optimal protein activity and/or reduce non-specific or background activity. Also reagents that otherwise improve the efficiency of the assay, such as protease inhibitors, nuclease inhibitors, anti-microbial agents, etc., may be used. The mixture of components may be added in any order that provides for the requisite activity.

X-GlcU and PNPG are used in an amount sufficient to produce a spectrophotometrically or visually detectable change in response to being cleaved by beta-glucuronidase enzyme, and is usually in the range of 10–150 μg/mL for X-GlcU and 100 μM–50 mM for PNPG, preferably about 50 μg/mL for X-GlcU and 1 mM for PNPG.

The buffer solution used in the assay may be any buffer which is used in a sufficient quantity to maintain the pH of the sample to be tested at about 3–5, preferably at pH 4.0. Preferably, the buffer is a mixture of $NaH_2PO_4$ and $Na_2HPO_4$, and is usually in the range of 0.05 to 1.5 M, preferably 1.0 M of sample, most preferably 0.1 M.

Spectrophotometric monitoring of the reaction mixture results in detection of a positive endpoint (i.e. increase in Absorbance of about 0.05 absorbance units) earlier than is possible for visual detection of the bright yellow color (PNPG) or detection of the bright blue color (X-GlcU) under long wave UV. Detection by visual or spectrophotometric methods can easily be accomplished within about 24 hours or less.

6. GUS Antibodies

Antibodies that specifically bind to the proteins of the present invention (i.e., antibodies which bind to a single antigenic site or epitope on the proteins) are useful for a variety of purposes, as described above.

Antibodies to GUS may be generated using methods that are well known in the art. Such antibodies may include, but are not limited to, polyclonal, monoclonal, chimeric, single chain, Fab fragments, and fragments produced by a Fab expression library.

For the production of antibodies, various hosts including goats, rabbits, rats, mice, humans, and others, may be immunized by injection with GUS or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to GUS have an amino acid sequence consisting of at least five amino acids and more preferably at least 10 amino acids. It is also preferable that they are identical to a portion of the amino acid sequence of the natural protein, and they may contain the entire amino acid sequence of a small, naturally-occurring molecule. Short stretches of GUS amino acids may be fused with those of another protein such as keyhole limpet hemocyanin and antibody produced against the chimeric molecule.

Monoclonal antibodies to GUS may be prepared using any technique which provides for the production of antibody molecules by continuous cell lines in culture. These include, but are not limited to, the hybridoma technique, the human B-cell hybridoma technique, and the EBV-hybridoma technique. See, e.g., Kohler, G. et al. (1975) *Nature*, 256, 495–497; Kozbor, D. et al. (1985) *J. Immunol. Methods* 81, 31–42; Cote, R. J. et al. (1983) *Proc. Natl. Acad. Sci. USA* 80, 2026–2030; Cole, S. P. et al. (1984) *Mol. Cell Biol.* 62,109–120.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between GUS and its specific antibody. A two-site, monoclonal-based immunoassay utilizing monoclonal antibodies reactive to two non-interfering GUS epitopes is preferred, but a competitive binding assay may also be employed (Maddox, supra).

Antibodies may be conjugated to a solid support suitable for an assay (e.g., beads, plates, slides or wells formed from materials such as latex or polystyrene) in accordance with known techniques, such as precipitation. Antibodies may likewise be conjugated to detectable groups such as radiolabels (e.g. $^{35}S$, $^{125}I$, $^{131}I$), enzyme labels (e.g., horseradish peroxidase, alkaline phosphatase), and fluorescent labels (e.g., fluorescein) in accordance with known techniques.

The present invention is explained in greater detail in the following non-limiting Examples.

EXAMPLE 1

Materials and Methods: Gene Isolation

Bacterial Strains and Plasmids.

*L. gasseri* was grown in MRS (Difco, Detroit, Mich.) at 37° C. *E. coli* strains were grown in Luria-Bertani (LB) broth at 37° C. with shaking or on LB broth supplemented with 1.5% agar.

DNA Manipulations.

*L. gasseri* ADH DNA was isolated as described previously (Walker and Klaenhammer, *J. Bacteriol.* 176:5330 (1994)). Standard protocols were used for routine isolation of plasmid DNA from *E. coli*, ligations, endonuclease restrictions, DNA modification and transformation (Sambrook et al., Molecular cloning: A laboratory manual, 2nd ed. (1989)). Plasmid DNA used for sequencing was isolated using the QIAprep spin kit per the manufacturer's instructions (QIAGEN Inc.). PCR was performed via standard protocols (Innis et al., PCR protocols: A guide to methods and applications, Academic Press 1990)). DNA sequencing on both strands of the template was performed with an ABI model 377 automated gene sequencer (Perkin-Elmer) or manually, with the ThermoSequenase™ kit (Amersham).

Gene isolation.

A plasmid library of randomly-sheared *L. gasseri* ADH genomic DNA, generated by nebulization of total genomic DNA, was T4 DNA Polymerase-treated to blunt the ends, and inserted into the SmaI site of pUC19. The resulting library was electroporated, using standard protocol, into supercompetent *E. coli* DH10B (Gibco BRL) for amplification of the library. The amplified library was isolated by standard methods and electroporated into the GUS non-producing *E. coli* strain KW1 (Wilson et al. (1995) *Microbiology* 141:1691) and screened for complementation of GUS activity. A GUS-positive clone was identified on LB plates containing 50 µg/mL X-GlcU+200 µg/mL carbenicillin. The plasmid DNA insert from the GUS-producing isolate was completely sequenced and shown to encode two complete open reading frames (ORFs). The first ORF, designated gusA, is a 1797 nucleotide ORF encoding a 598 amino acid protein sharing 39% identity with the *E. coli* GusA protein. The second ORF, designated ORF-R encodes a protein with weak homology to at least two classes of transcriptional activators from many other bacteria, and may play a role in the regulation of the gusA gene.

The gusA gene appears to consist of its own promoter region and terminator structure and the transcript is transcribed as a monocistronic unit. FIG. 1 depicts the genomic locus of the gusA gene. The GC content of the *L. gasseri* ADH gusA gene (34.25%) indicates that it evolved separately from the *E. coli* gusA gene (52.2% GC). Three out of the 15 amino acids comprising the active-site signature-sequence of the *L. gasseri* ADH GUS enzyme differ from other previously identified GUS enzymes.

Construction of the Expression Vector pTRK664.

Plasmid pTRK563 was created by the ligation of a BglII-NheI PCR product amplified from pGK12 with primers 5'-AGTC<u>AGATCT</u>ACAGCTCCAGATCGATTCAC-3' (SEQ ID NO:3) and 5'-AGTC <u>GCTAGC</u>TTACGAACTGGCACAGATGG-3' (SEQ ID NO:4) to a BglII-NheI PCR product amplified from pBluescript II KS(+) with primers 5'-AGTC<u>AGATCT</u>TTAAT GCGCCGCTACAGG-3' (SEQ ID NO:5) and 5'-AGTC <u>GCTAGC</u>AATGCAGCAGCTGGCA CGACAGG-3' (SEQ ID NO:6) (restriction sites are underlined). For the creation of plasmid pTRK664, the T7 terminator, Lactobacillus P6 promoter, and gusA gene were cloned sequentially into plasmid pTRK563. The T7 terminator was amplified from pET28a(+)as an XhoI-SalI fragment as described previously (Walker and Klaenhammer (2000) *Appl. Environ. Microbiol.* 66:310–319) and cloned into the SalI site. The Lactobacillus P6 promoter was amplified from pLA6 (Djordjevic et al. (1997) *Can. J. Microbiol.* 43:61–69) using the primers 5'-AGA<u>GTCGAC</u>TAATGAAGCTTGTTTTGTT TCAG-3' (SEQ ID NO:7) and 5'-ACT <u>GAATTC</u>TTCTTTAGTTAATGGCTCAG-3' (SEQ ID NO:8) and cloned as a SalI-EcoRI fragment. The gusA gene including the putative RBS was am-plified using the primers 5'-GTC<u>GAATTC</u>TACTAGAAAGGAAAATCATC-3' (SEQ ID NO:9) and 5'-TGC <u>TCTAGA</u>TAATTGAGCACGATTATTTG-3' (SEQ ID NO:10) and cloned as an EcoRI-XbaI fragment.

Expression of gusA in *E. coli*.

In order to create the plasmid pTRK665, the gusA gene was amplified using the primers GUS7F 5'-AG TC<u>CATGG</u>AATCT GCACTATATCCAATTC-3' (SEQ ID NO:11) and GUS6R 5'-ACTG<u>GAATTC</u>TAATTGAGCA CGATTATTTG-3' (SEQ ID NO:12). An NcoI site (underlined) was designed in primer GUS7F to include the start codon sequence. Cloning into the NcoI-EcoRI sites of pET28a(+) resulted in the translational fusion of the gusA gene to the T7 promoter and *E. coli* ribosome binding site of the plasmid. Plasmid pTRK665 was created in *E. Coli* DH5α and transformed into *E. coli* Tuner(DE3) to perform the induction experiments. For induction experiments, cells at an $OD_{600}$ of 0.6 were induced with 1.0 mM isopropyl-β-D-thiogalactopyranoside (IPTG) for 4 h. Samples were removed at appropriate time points to measure growth and β-glucuronidase activity.

Enzyme Characterization.

For lactobacilli, β-glucuronidase activity in cell extracts (CFEs) was measured by the hydrolysis of para-nitrophenyl-β-D-glucuronide (PNPG) (Sigma, St. Louis, Mo.). Cultures (10.0 ml each) were washed twice in 10.0 ml of GUS buffer (sodium phosphate buffer (1.0 M or 0.1 M)–2.5 mM EDTA [pH 6.0]) and resuspended in 1.0 ml of the same. Cell suspensions were then added to chilled tubes with silica beads and subjected to three 1-min cycles at the highest setting in a Mini Bead Beater (Biospec Products, Bartlesville, Okla.) with 1 min on ice in between cycles. Following centrifugation to pellet beads and cell debris, the CFE was collected and kept temporarily on ice until the start of the assays. Protein concentrations were determined by the method of Bradford (Bradford (1976) *Anal. Biochem.* 72:248–254) using the Sigma protein determination kit.

Figure 2:
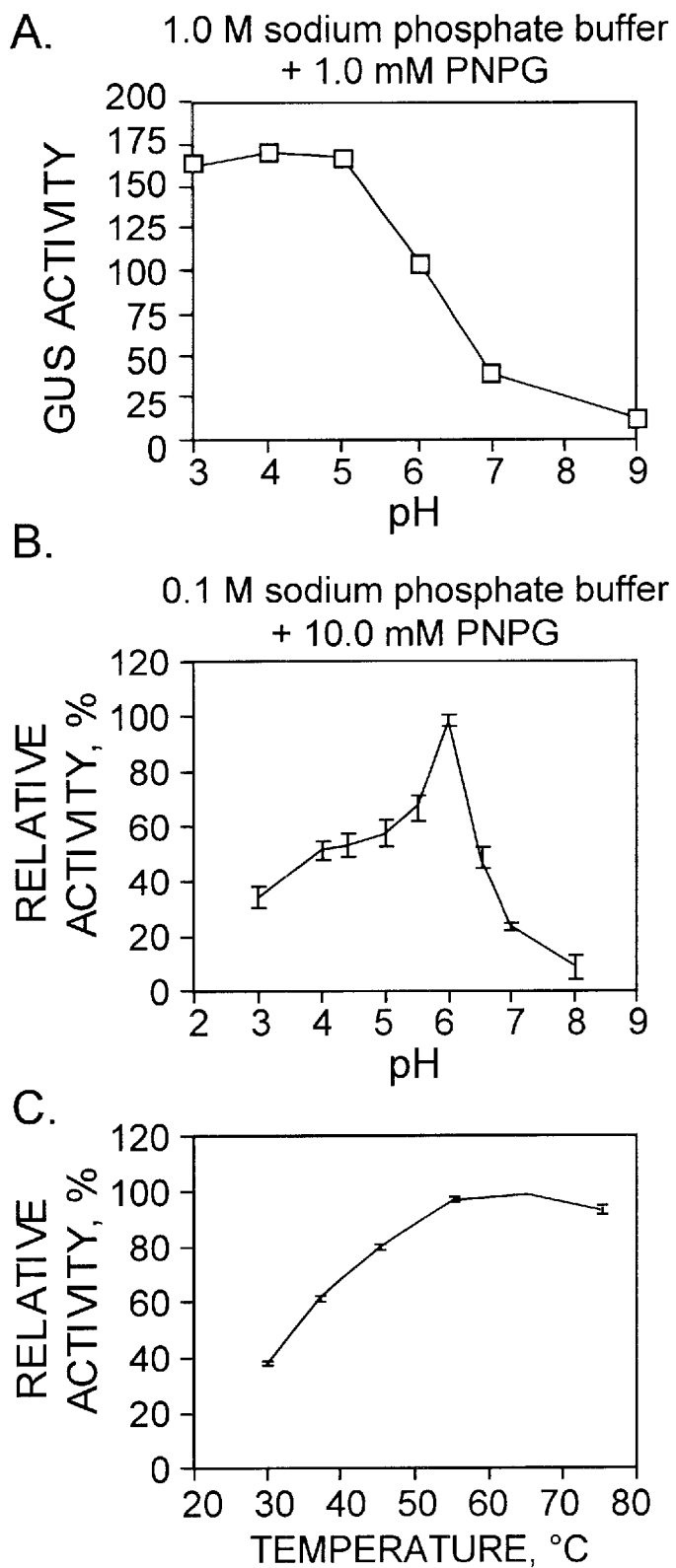
FIGS. 2A–2C demonstrate the effect pH (A, B) and temperature (C) on β-glucuronidase activity. CFEs of late-log-phase *L. gasserii* ATCC 33323 cells harboring plasmid pTRK664 were assayed under various conditions for the hydrolysis of PNPG. pH experiments were performed in the presence of 1.0 M sodium phosphate buffer and 1.0 mM PNPG (A) or 0.1 M sodium phosphate buffer and 10.0 mM PNPG (B) at 37° C., and temperature experiments were performed at pH 6.0 (C). GUS activity in A is expressed in nmol·min$^{-1}$·mg$^{-1}$.

For pH optima determination, two independent assays conditions were used that used different concentrations of sodium phosphate buffer and PNPG. The first assay was conducted in 1.0 M sodium phosphate buffer with the final concentration of 1.0 mM PNPG (FIG. 2A). The second assay was performed in 0.1 M sodium phosphate buffer with a final concentration of 10.0 mM PNPG (FIG. 2B).

CFEs were warmed to the assay temperature and 200 µl of sample was added to 800 µl of GUS buffer containing PNPG and incubated at 37° C. (except during temperature experiments). The pH of the GUS buffer was 6.0 except during pH experiments, when sodium phosphate buffer at different pHs was used to prepare the GUS buffer. At appropriate time intervals, usually 5, 10, and 15 min, 100 µl of the reaction mixture was added to 800 µl of 1.0 M $Na_2CO_3$, and the optical density was measured at 405 nm ($OD_{405}$). One unit of activity is defined as 1 nmol of p-nitrophenol liberated per min per milligram of protein. For the measurement of activity in *E. coli* cells, assays were performed nearly identically, except that whole cells disrupted with chloroform were used instead of cell extracts and assays were done at a pH of 4.0 to reduce any potential interference by the native *E. coil* β-glucuronidase. Enzyme activity for *E. coli* experiments is represented per $OD_{600}$. Each value presented is the average of results from at least three independent experiments.

Figure 3:
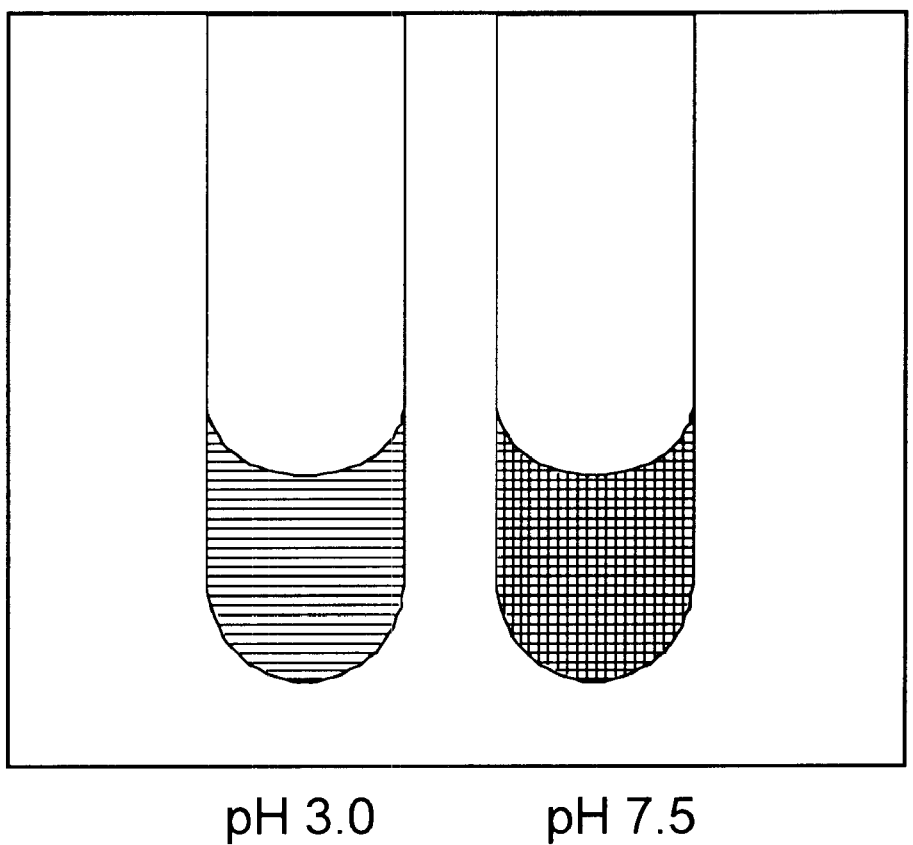
FIG. 3 demonstrates the effect of pH on *L. gasseri* ADH GUS activity when the enzyme is expressed in an *E. coli* host strain. Cells were incubated in the presence of 20 μg/mL of X-GlcU at either pH 3.0 (left) or at pH 7.5 (right).

To better characterize the gusA gene and determine whether it could be expressed in other GUS-non-producing bacteria, the gusA gene was transformed and expressed, as determined by GUS activity, in three different *E. coli* strains (DH10B, KW1, and Tuner (DE3) (Novagen)), *L. acidophilus* NCFM (ATCC 700396), and *L. gasseri* ATCC 33323. Using the *L. gasseri* ATCC 33323 strain expressing *L. gasseri* ADH GUS, the optimal pH range of the GUS enzyme was determined. Using 1.0 M sodium phosphate buffer and 1.0 mM PNPG, it was observed that *L. gasseri* ADH GUS was most active at low pH, exhibiting optimum activity near pH 4.0 and retaining greater than 95% of its activity at pH 3.0 (FIG. 2A). Using 0.1 M sodium phosphate buffer with 10.0 mM PNPG, the activity dropped off quickly at pH values above 6.0, but the enzyme retained more than 50% activity at a pH of 4.0 and approximately 33% activity at pH 3.0 (FIG. 2B). Lower pH conditions were not tested. The differenced observed between the data presented in FIG. 2A and FIG. 2B can be attributed to the differences in the buffering capacity of the buffer (1.0 M vs. 0.1 M sodium phosphate buffer) and the final concentration of PNPG which is an acid. Similar to the *L. gasseri* ADH GUS expressed in *L. gasseri* ATCC 33323, *L. gasseri* ADH GUS activity was dimished at pH 7.5 (right test tube, yellow coloration) as compared to pH 3.0 (right test tube, blue coloration) when the enzyme was expressed in an *E. coli* host strain (FIG. 3).

CFEs of *L. gasseri* ATCC 33323 cells harboring plasmid pTRK664 were also used to measure the effects of temperature and saccharic acid 1,4-lactone on β-glucuronidase activity. FIG. 2C shows the results of temperature optimization experiments. The maximum activity was found at approximately 65° C. An approximately two-fold increase in activity was observed as the temperature was raised from 37 to 65° C.

Saccharic acid 1,4-lactone (SAL) is a specific inhibitor of all β-glucuronidases examined to date from *E. coli*, plants, and mammals (Gottschalk et al. (1996) *Appl. Microbiol. Biotechnol.* 45:240–244). To determine the sensitivity of *L. gasseri* GusA to SAL, β-glucuronidase assays were performed on CFEs in the presence of 0.5 or 1.0 mM SAL at 37° C. and pH 6.0. The addition of 0.5 or 1.0 mM SAL resulted in the reduction of β-glucuronidase activity of the cell extracts by 80 and 88%, respectively.

Controlled Expression of gusA in *E. coli*.

Figure 4:
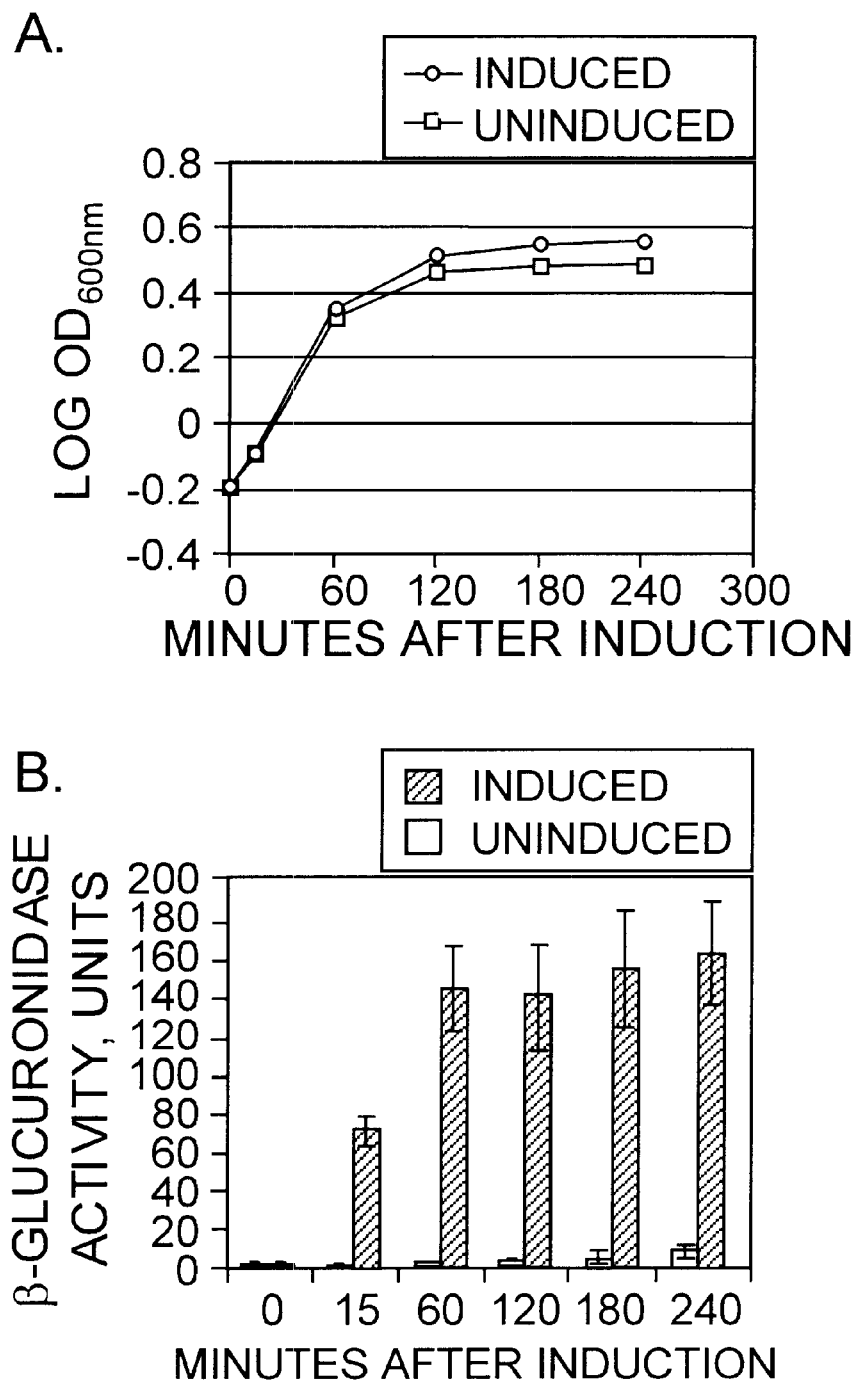
FIGS. 4A and 4B show growth (A) and expression (B) of β-glucuronidase for *E. coli* Tuner(DE3)::pTRK665 cells following induction with 1.0 mM IPTG.

In order to further correlate β-glucuronidase activity with gusA expression, plasmid pTRK665 was constructed to contain a translational fusion between the gusA gene and the T7 promoter and ribosome binding site of pET28a(+). Plasmid pTRK665 was transformed into *E. coli* Tuner (DE3), which carries a chromosomal copy of the T7 polymerase gene under the control of the inducible lac promoter. GusA expression was induced in *E. coli* Tuner(DE3):: pTRK665 over 4 h by the addition of 1.0 mM IPTG (FIG. 4). β-Glucuronidase activity peaked in induced cells between 15 and 60 min and stayed relatively constant over the time course of 4 h. The growth of induced cells was not significantly different from that of uninduced cells.

EXAMPLE 2

GUS Activity in *Lactobacillus gasseri*

To determine if GUS activity could be found in *Lactobacillus gasseri* isolates other than ADH, GUS activity was tested in 12 other *Lactobacillus gasseri* isolates, including ATCC 33323, NCK 1340, NCK 1344, NCK 1345, NCK 1342, NCK 1341, NCK 1346, NCK 1347, NCK 1348, NCK 1349, NCK 1343, NCK 1338. It was observed that 6 out of 12 *Lactobacillus gasseri* isolates tested, including NCK 1344, NCK 1345, NCK 1347, NCK 1348, NCK 1349, and NCK 1343 contained GUS activity. To determine if the GUS activity detected in these isolates correlated with the presence of a gusA gene, PCR amplification, with primers GUS-1F (SEQ ID NO:13) and GUS-1R (SEQ ID NO:14) designed to the *Lactobacillus gasseri* ADH gusA locus, was performed on the *Lactobacillus gasseri* isolates. PCR primer annealing temperature was 50° C. An amplicon, of identical molecular weight to the *L. gasseri* ADH gusA, was amplified from 4 of the 12 other *Lactobacillus gasseri* isolates, including NCK 1344, NCK 1348, NCK 1349, and NCK 1343. Isolates NCK 1345 and NCK 1347, which had detectable GUS activity but no gusA amplicon, may have had base pair changes in one or more nucleotides at the site where the PCR primers would anneal therefore decreasing primer binding.

Figure 5:
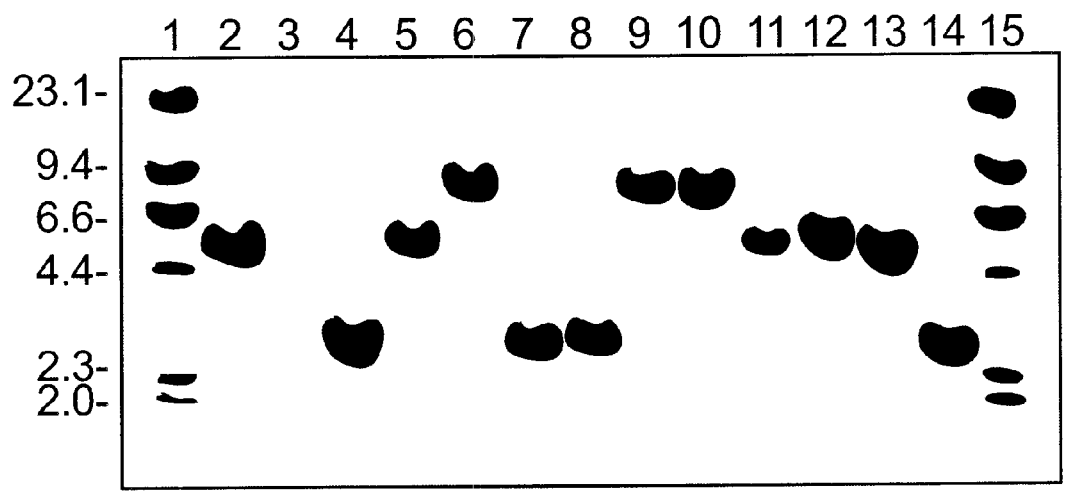
FIG. 5 shows Southern hybridization of genomic DNA from *L. gasseri* strains. Genomic DNA from each strain was digested with EcoRI, separated on a 1.0% agarose gel, and transferred to a nylon membrane prior to hybridization with the gusA probe. Lanes: 1 and 15, DIG-labeled molecular weight marker; 2, strain ADH; 3, ATCC 33323; 4, NCK 1340; 5, NCK 1344; 6, NCK 1345; 7, NCK 1342; 8, NCK 1341; 9, NCK 1346; 10, NCK 1347; 11, NCK 1348; 12, NCK 1349; 13, NCK 1343; 14, NCK 1338. Sizes of the molecular weight marker bands are indicated in kilobases.

In addition to PCR amplification, the distribution of gusA genes among *L. gasseri* strains was evalutated by Southern blot analysis using a digoxigenin-labeled 776-bp internal region of the gusA gene generated with primers GUS-1F (SEQ ID NO:13) and GUS-1R (SEQ ID NO:14). Genomic digests from each of the strains were separated by electrophoresis and transferred to a nylon membrane. The membrane was then hybridized at mild stringency with the labeled gusA probe. With the exception of ATCC 33323, all of the strains tested showed a positive hybridization to the gusA probe (FIG. 5).

EXAMPLE 3

Active *L. gasseri* GUS Can Be Efficiently Expressed in a Variety of Lactobacilli and *Streptococcus thermophilus*

While the *E. coli* gusA gene has been used successfully as a reporter gene in a variety of organisms, a number of researchers have reported diminished or no activity in a number of Lactobacillus species including *L. helveticus* (Kleerebezem et al., *Appl Environ Microbiol* 63:11 (1997)), *L. gasseri* and *L. plantarum* (Kahala and Palva, *Appl Microbiol Biotechnol* 51 (1999)) and *L. sakei* (Stentz et al., *Appl Environ Microbiol* 66:10 (2000)). While the reasons for this poor performance is not yet known, in some cases, the loss of β-glucuronidase activity in the cells could be correlated with a drop in pH. To illustrate the utility of the *L. gasseri* gusA gene specifically in lactic acid bacteria, three separate *Lactobacillus acidophilus* promoters were used to demonstrate that *L. gasseri* GUS can be efficiently expressed and is active in a variety of lactobacilli and *Streptococcus thermophilus*.

Materials and Methods.

Growth of bacterial strains, DNA isolation and manipulations, transformations and enzyme assays were all performed as described previously (Russell and Klaenhammer, *Appl Environ Microbiol* 67:3 (2001)).

Construction of Plasmids.

Plasmid pTRK563 is a low-copy, broad-host range plasmid that contains the pWV01 replicon, an erythromycin resistance gene and an *E. coli* lacZ complementation cassette (see EXAMPLE 1). To create the promoter-probe vector pWMR33, the *L. gasseri* gusA gene and the *Lactobacillus johnsonii* lactacin F operon transcriptional terminator were cloned into plasmid pTRK563. The gusA gene was amplified from *L. gasseri* chromosomal DNA by PCR using the primers 5'-GTCGAATTCTACTAGAAAGGAAAATCATC-3' (SEQ ID NO:15) and 5'-TGCTCTAGATAATTGAGCACGATTATTTG-3' (SEQ ID NO: 16), digested with EcoRI and XbaI and ligated to pTRK563 digested with the same enzymes. To inhibit read-through transcription of gusA from plasmid-derived sequences, the lactacin F terminator (Fremaux et al., *Appl Environ Microbiol* 59:11 (1993)) was amplified from *L. johnsonii* chromosomal DNA with the primers 5'-ACTGGCTAGCAACAGATCTTGGTTATAC-3' (SEQ ID NO:17) and ACTGCTCGAGTTTATCAGGTTCAAAATTTC-3' (SEQ ID NO:18), digested with NheI and XhoI and ligated to pTRK563::gusA digested with the same enzymes. Plasmids pWMR35, pWMR36 and pWMR38 were then created by cloning the *L. acidophilus* P6 (Djordjevic et al., *Can J Microbiol* 43 (1997), phoH and P311 (Kullen and Klaenhammer, *Mol Microbiol* 33:6 (1999)) promoters, respectively, into the SalI-EcoRI sites of pWMR33.

Results.

In order to test the ability of GusA to be expressed in a variety of lactic acid bacteria, plasmids pWMR33, pWMR35, pWMR36 and pWMR38 were transformed into the organisms shown in TABLE 1. GUS activity was measured in CFE's of all organisms during mid-log-phase growth (O.D.$_{600}$=0.6). Previously, using the *E. coli* gusA gene, the highest reported activity in a Lactobacillus species has been 301 U using the *Lactococcus lactis* lacA promoter (Platteeuw et al., *Appl Environ Microbiol* 60, 2 (1994). However, using the *L. gasseri* gusA gene, activities as high as 9725 U could be detected (TABLE 1). Higher activities could be routinely detected from overnight cultures (data not shown). High activities could be measured from promoter containing constructs in all of the organisms tested. These results indicate that in a number of lactobacilli and in *S. thermophilus*, *L. gasseri* GUS can be efficiently used as a reporter of gene expression.

TABLE 1

| Bacterium | β-Glucuronidase Activity (mean ± SD) | | | |
|---|---|---|---|---|
| | pWMR33 | pWMR35 | pWMR36 | pWMR38 |
| L. acidophilus | 13.9 ± 2.3 | 6489 ± 1271 | 9049 ± 734 | 4270 ± 1171 |
| L. gasseri | 12.4 ± 4.2 | 2801 ± 695 | 5763 ± 620 | 4976 ± 383 |
| L. johnsonii | 13.4 ± 0.2 | 6611 ± 2456 | 4070 ± 1716 | 938 ± 511 |
| L. helveticus | 9.9 ± 2.3 | 2488 ± n/a | 9725 ± 1924 | 3625 ± 155 |
| L. plantarum | 6.8 ± 4.3 | 7047 ± 1016 | 6423 ± 346 | 3745 ± 595 |
| S. thermophilus | 1.2 ± .15 | 3802 ± 162 | 1778 ± 359 | 127 ± 1.5 |

EXAMPLE 4

Utility of *L. gasseri* GUS to that of *E. coli* GUS for Measuring Promoter Activity in *L. gasseri* ATCC33323

Materials and Methods.

Growth of bacterial strains, DNA isolation and manipulations, transformations and *L. gasseri* GUS assays were all performed as described previously (Russell and Klaenhammer, *Appl. Environ. Microbiol.* 67:1253–1261 (2001)). *E. coli* GUS assays were performed as described by Wilson et al.(*GUS Protocols*, Acad. Press, San Diego, Calif., (1992)).

Construction of Plasmids.

Plasmid pWMR35 was constructed as described in study EXAMPLE 3. A similar vector, plasmid pWMR39 was created which differed only in that it contained the *E. coli* gusA gene in place of the *L. gasseri* gusA gene. An additional plasmid, pTRK570, was used which contained the *E. coli* gusA gene expressed from the P6 promoter on the high-copy shuttle vector pTRKH2 (O'Sullivan and Klaenhammer, *Gene* 137 (1993).

Results.

Plasmids pWMR36 and pWMR39 are both low-copy number vectors which contain the P6 promoter driving expression of either the *L. gasseri* or the *E. coli* gusA gene. *E. coli* transformants of both plasmids showed GUS activity as observed by blue colonies on BHI/X-glu plates. However, only plasmid pWMR35 gave rise to blue colonies in *L. gasseri* ATCC33323 plated on MRS/X-glu plates. Log-phase cultures containing each of the plasmids were assayed for GUS activity. Only 18.9 U of activity could be detected from *L. gasseri*::pWMR39, compared with 2801 U from *L. gasseri*::pWMR35. In an attempt to increase the amount of *E. coli* GUS being detected from *L. gasseri* cells, pTRK570, a high-copy vector containing the P6 promoter and *E. coli* gusA gene, was transformed into *L. gasseri* ATCC33323. Transformants plated on MRS/X-glu were a mixture of white and blue colonies. Both types of colonies, when replated, gave rise again to white and blue colonies, indicating that instability or loss of the plasmid DNA was not the cause of white colonies. Only 577.9 U of activity could be detected from log-phase *L. gasseri*::pTRK570 cultures, still only approximately one-fifth the activity expressed by *L. gasseri* containing the Lactobacillus GUS expressed from a lower copy-number plasmid. These data support the use of the *L. gasseri* gusA gene as a more efficient reporter of gene expression than the *E. coli* gusA gene.

Figure 6:
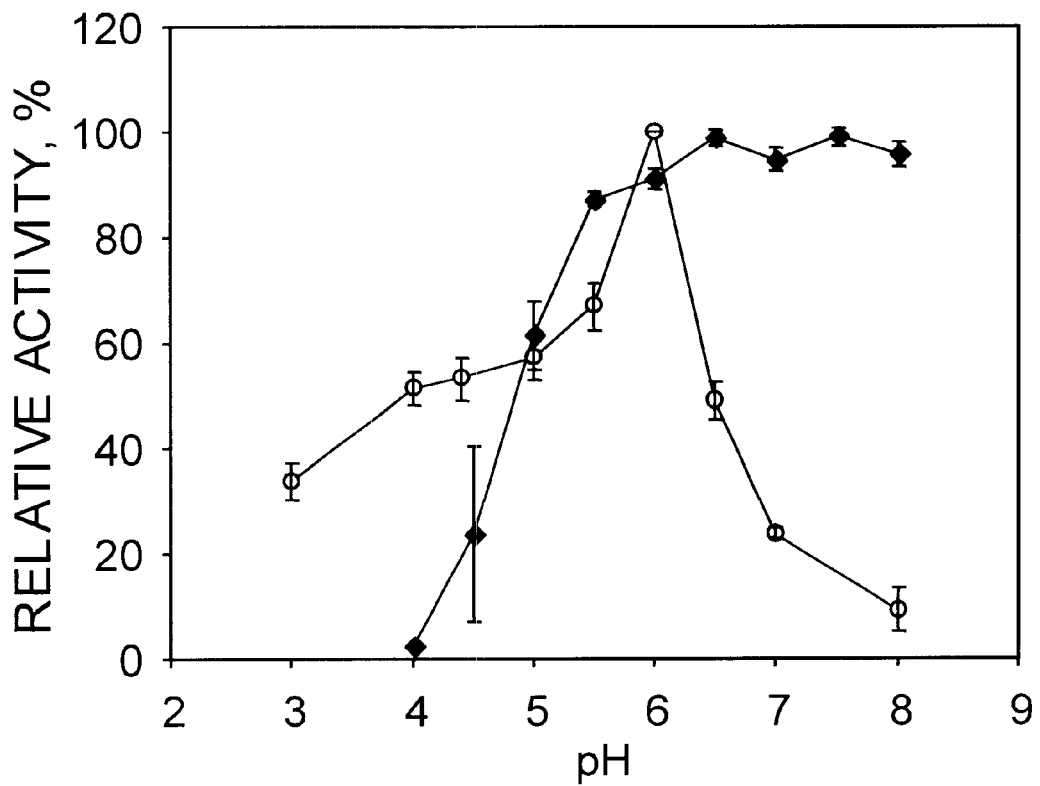
FIG. 6 shows GUS activity, measured by hydrolysis of PNPG, in cell-free extracts of *L. gasseri*::pWMR35 (open circles) and *L. gasseri*::pWMR39 (diamonds) that were at different pHs.

In order to compare the functional pH ranges of the *L. gasseri* and the *E. coli* GUS enzymes, cell-free extracts from log-phase *L. gasseri*::pWMR35 and *L. gasseri*::pTRK570 were assayed in buffers at various pH's (FIG. 6). The results show that the *L. gasseri* GUS can be detected preferentially at acidic pH's, while only the *E. coli* enzyme is detectable in the alkaline range. These data support the use of the *L. gasseri* GUS in applications where acidity may be inhibitory to other reporter enzymes like green fluorescent protein or *E. coli* GUS.

In addition, the use of *L. gasseri* GUS as a food grade marker is supported by its inactivity at colonic pH ranges, typically in the neutral range in the small intestin. The data on GUS from *L. gasseri*, suggest that the Lactobacillus enzyme would not be active in vivo. At physiological pH ranges, the enterobacterial enzyme would appear to be the major contributor to colonic β-glucuronidase activity. The relative activities of the two GUS enzymes at varying pH appears consistent with the observations of Pedrosa, Golner, Bolding, Barakat, Dallal, and Russell (*Am. J. Clin.Nutr* 61:353–359; 1995) that feeding of elderly subjects with live cells of GUS+ *L. gasseri* ADH, significantly lowered the total level of B-glucuronidase assayed in the fecal contents. The collective data, therefore, suggests that feeding ADH lowered the major GUS activity contributed by *E. coli*.

The foregoing is illustrative of the present invention, and is not to be construed as limiting thereof. The invention is defined by the following claims, with equivalents of the claims to be included therein.

That which is claimed is:

1. An isolated nucleic acid encoding β-glucuronidase (GUS), said isolated nucleic acid selected from the group consisting of:
   (a) a DNA having the nucleotide sequence given herein as SEQ ID NO:1;
   (b) a polynucleotide that hybridizes to the DNA of (a) above under stringent conditions represented by a wash stringency of 50% Formamide with 5×Denhardt's solution, 0.5% SDS and 1×SSPE at 42° C., and which encodes a β-glucuronidase (GUS) protein; and
   (c) a polynucleotide that differs from the DNA of (a) or the polynucleotide of (b) above due to the degeneracy of the genetic code, and which encodes the protein encoded by the DNA of (a) or the polynucleotide of (b) above.

2. An isolated nucleic acid according to claim 1 encoding a GUS protein having a peak activity at a pH of from 3 to 5 in 1.0 M sodium phosphate buffer using 1.0 mM PNPG substrate concentration.

3. An isolated nucleic acid according to claim 1 which encodes a protein having the amino acid sequence given herein as SEQ ID NO:2.

4. A recombinant nucleic acid comprising a promoter operably linked to an isolated nucleic acid encoding a GUS according to claim 1.

5. A vector comprising an isolated nucleic acid according to claim 1.

6. The vector according to claim 5, wherein said vector is a plasmid.

7. The vector according to claim 5, wherein said vector is an Agrobacterium vector.

8. A host cell containing an isolated nucleic acid according to claim 1 and expressing the encoded GUS protein.

9. The host cell according to claim 8, wherein said host cell is a plant cell.

10. The host cell according to claim 8, wherein said host cell is an animal cell.

11. The host cell according to claim 8, wherein said host cell is a yeast cell.

12. The host cell according to claim 8, wherein said host cell is a bacterial cell.

13. The host cell according to claim 8, wherein said host cell is a lactic acid bacteria cell.

14. A method of making a recombinant cell, comprising transforming a host cell with a vector according to claim 7.

15. The method according to claim 14, further comprising the step of expressing the encoded GUS protein in said host cell.

16. The method according to claim 15, further comprising the step of detecting said encoded GUS protein in said host cell.

17. The method according to claim 15, further comprising the step of collecting said encoded GUS protein from said host cell.

* * * * *